United States Patent [19]

Davis et al.

[11] Patent Number: 5,170,567
[45] Date of Patent: Dec. 15, 1992

[54] ELECTRONIC INCLINOMETER

[75] Inventors: Kelvin R. Davis, Stilton; Stephen J. Bates, Godmanchester; Andrew J. Murray, Southoe, all of United Kingdom

[73] Assignee: The Stanley Works, New Britain, Conn.

[21] Appl. No.: 223,241
[22] PCT Filed: Jan. 23, 1987
[86] PCT No.: PCT/GB87/00041
§ 371 Date: Nov. 1, 1990
§ 102(e) Date: Nov. 1, 1990
[87] PCT Pub. No.: WO87/04514
PCT Pub. Date: Jul. 30, 1987

[30] Foreign Application Priority Data

Jan. 23, 1986 [GB] United Kingdom ............... 8691586

[51] Int. Cl.5 ................................................ G01C 9/00
[52] U.S. Cl. ........................................ 33/366; 33/377
[58] Field of Search ................... 33/366, 377, 365; 73/708, 724, 729

[56] References Cited

U.S. PATENT DOCUMENTS 2,584,917  2/1952  Powell ................... 33/377
3,906,471  9/1975  Shawhan ................. 33/366 X
4,028,815  6/1977  Buckley et al. ........... 33/366

FOREIGN PATENT DOCUMENTS

2048473  5/1979  United Kingdom .
2071887  12/1979  United Kingdom .
2070774  9/1981  United Kingdom ............... 33/365

Primary Examiner—Harry N. Haroian
Attorney, Agent, or Firm—Chilton, Alix & Van Kirk

[57] ABSTRACT

A sensor for an incination measuring device which comprises a capsule (3) part-filled with a conductive liquid. First to fourth electrodes (A-D) are disposed within the capsule in contact with the liquid. An electrical signal is applied between electrodes (C, D) and one then the other of electrodes (A, B), to derive a signal indicative of the degree of immersion of the electrode (A), and then the electrode (B) within the liquid. The ratio of these signals is related to the angle of inclination of the capsule about the reference axis (O) and relative to a first reference angle defined at the gap between the electrodes (A, B). The capsule (1) is also constructed to compensate for thermal effects, by forming the sides of the capsule so that they are responsive to pressure change within the capsule caused by thermal expansion of the contents of the capsule to expand the volume of the capsule, to keep the level of liquid therein constant.

44 Claims, 5 Drawing Sheets

UNIFORM INTERNAL PRESSURE = P

SIMPLE-SUPPORT AROUND CIRCUMFERNCE

NOTATION FOR GEOMETRY OF FLAT CIRCULAR PLATE UNDER UNIFORM PRESSURE
(DEFLECTION EXAGGERATED FOR CLARITY)

FIG. 9.

ELECTRONIC INCLINOMETER

This invention relates to a device and, more particularly, but not exclusively to a sensor for an electronic level or inclination gauge.

Optical levels, more commonly called spirit levels, are well known and provide an optical indication of whether or not a surface is horizontal, based on the principle of an air bubble in a liquid-filled vial always seeking the highest point in the vial, the vial being slightly curved so that when at level, the bubble will always take up an equilibrium position. Such bubble levels, if disposed in a suitable frame, can also be used to provide an indication of whether or not a surface is vertical.

However, such spirit levels are not capable of measuring deviations from horizontal or vertical outside a very limited range. Also, such spirit levels can be difficult to read accurately as the measurement of level or plumb depends on the ability of the user to determine the position of the bubble. Factors such as poor lighting or poor eyesight obviously affect this.

Electronic spirit levels have been proposed, for example by Cantarella, in U.S. Pat. No. 4,167,818, which uses a capsule part-filled with a conductive liquid. Several electrodes are disposed within the capsule, the resistance between the electrodes being dependent on the position of the liquid within the capsule which, in turn, is dependent upon its inclination. A digital readout of angles of inclination from level and from plumb is provided. However such levels suffer the disadvantage that the accuracy of any measurement from horizontal or vertical is dependent upon ambient conditions such as temperature, as fluctuations in temperature will lead to variations in the level and resistance of liquid within the capsule which in turn will affect the reading of inclination for angles for which the electrodes are not equally immersed in the liquid.

According to the invention in a first aspect there is provided a capsule, part filled with a liquid, the volume of the liquid varying as a function of temperature and the capsule being elastically deformable in response to temperature-induced pressure change within the capsule, so that the internal volume of the capsule is variable in dependence upon temperature and whereby dimensions and material of walls of the capsule are selected to provide a predetermined relationship between the level of liquid within the capsule and temperature.

According to the invention, in a second aspect there is provided a capsule, part-filled with a liquid, the walls or the capsule being formed so that a temperature-induced pressure change within the capsule will cause the walls of the capsule to deform elastically to maintain the level of the liquid in the capsule substantially constant.

In the described embodiment of the invention a cylindrical capsule is provided, the bulging of the radial walls of the capsule in response to increased pressure within the capsule being chosen, by selecting the thickness and material for the radial walls, so that temperature induced increase in volume of the liquid is compensated by increased volume of the capsule, brought about by the change in configuration of the capsule radial walls, to maintain the liquid level substantially constant.

Alternatively, the change in configuration of the capsule radial walls is selected so that the liquid level fluctuates with temperature in a predetermined way.

In a particular application described, the capsule is used in an inclination measuring device in which measured resistances between electrodes disposed in the capsule and the liquid are dependent on inclination and prone to fluctuation with temperature, due to changes in liquid level within the capsule and also due to fluctuations in the resistance of switches connected to the electrodes in relation to the resistance of the liquid. The fluctuations due to liquid level may be compensated for by adjusting the volume of the capsule in the manner mentioned above. However, by allowing the volume of the capsule to change in a predetermined way which allows the level to fluctuate in a predicted manner, the temperature dependence of the resistance of the switches and liquid may be compensated for together with compensation for the change in liquid level, at least to a "best fit" approximation.

According to the invention in a third aspect there is provided a method of calibrating in inclination sensor of the form comprising a capsule part filled with a liquid, the position of the liquid within the capsule being indicative of the angle of rotation of the capsule about a reference axis, a plurality of electrodes disposed within the capsule for sensing said position within an angular range, an excitation source, a sensing circuit and means for connecting said electrodes to the sensing circuit and to the excitation source allow measurement of a plurality of electrical characteristics of the liquid which together are indicative of said position, said method comprising the steps of placing the sensor at at least two known angles $\theta$, measuring the corresponding sensed angles $\theta'$ and calculating from the known and sensed angles calibration values a and b where;

$$\theta = a\theta' + b$$

An embodiment of the invention will now be described, by way of example, with reference to the accompanying drawings, in which:

FIG. 3 is an exploded sectional view taken through the plane III-III' of FIG. 1;

Figure 1:
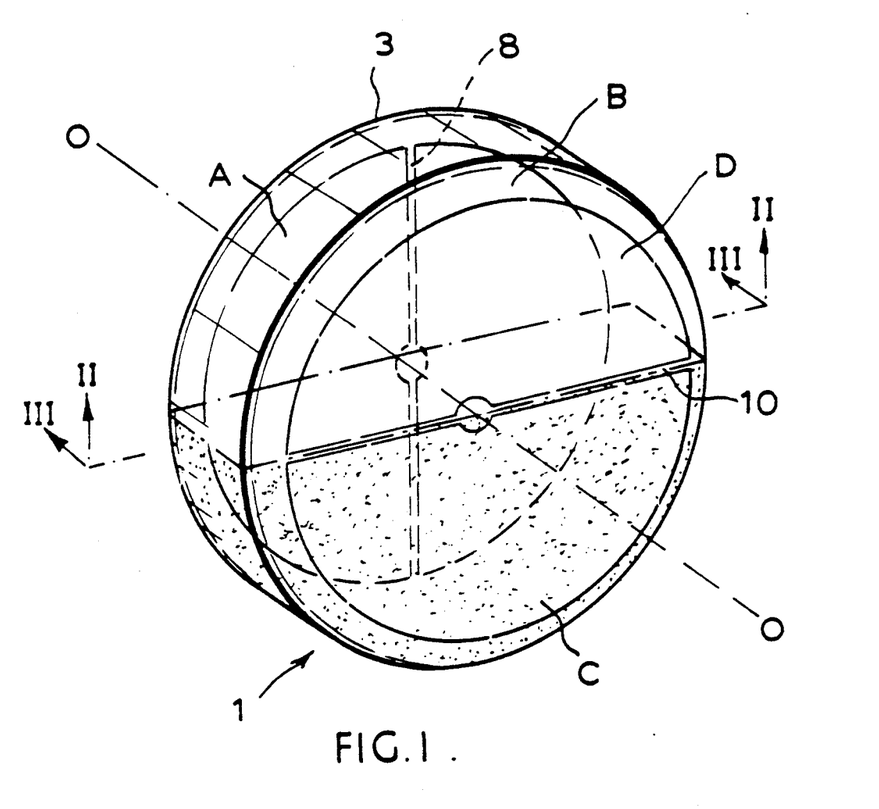
FIG. 1 is a perspective view of a sensor capsule forming part of an embodiment of the invention.
Figure 2:
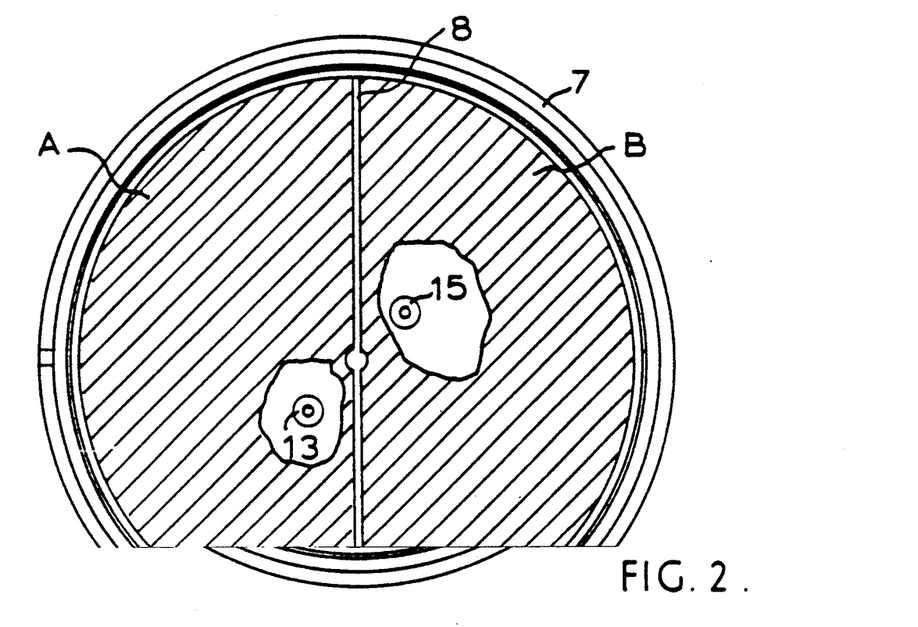
FIG. 2 is a sectional view taken in the plane II-II' of FIG. 1.

Referring to FIGS. 1 to 3, an inclination sensor, generally designated 1 is shown. The sensor comprises a capsule 3 of generally cylindrical form. The capsule 3 is formed from two engageable non-conductive chemically inert plastics mouldings 5,7 formed preferably from thermoplastic polyester (e.g. a polybutylene terephthalate (PBT) for example VALOX) reinforced with 15-20% glass beads to provide strength and stability.

The mouldings 5, 7 are ultra-sonically welded together to ensure a hermetic seal. The end faces 9,11 of the mouldings 5,7 are formed of a thickness so as to be elastically deformable in response to pressure variations within the capsule 3, as described hereinafter.

Within mouldings 5,7, electrodes A,B and C,D formed from nickel are respectively disposed. Each electrode A-D is of generally semi-circular form and is formed on its respective moulding 5,7 preferably by vacuum deposition or hot foil blocking (although it is to be appreciated that other electrode-forming methods may be employed). The electrodes A,B (or C,D) are separated one from the other by an elongate gap 8 (or 10) so that the electrodes A,B or C,D are not in direct electrical contact. The gaps 8,10 should be narrow, preferably less than 0.5 mm. Connections to the electrodes A-D are provided by means of rivets formed from conductive plastics material, which are bonded, preferably by ultra-sonically welding to the case halves; rivets 13,15 for electrodes A,B are shown in FIG. 2.

Alternatively, the capsule may be formed from two identical plastics discs, the electrodes being formed on the discs by silk screen printing, each disc then being connected to an open axial end of a hollow cylindrical plastics spacer, to form the capsule, the discs being rotated by 90° relative to one another to give the desired electrode configuration shown in FIG. 1.

The electrodes A,B are rotated by 90° about a reference axis O of the capsule with respect to the electrodes C,D to allow measurement of angles through 360° as described hereinafter. A conductive liquid 17 is disposed within the capsule 3, preferably a mixture of distilled water and methanol and a salt, for example sodium acetate trihydrate (CH₃ COONa 3H₂O), the capsule 3 being filled, at NTP to half its volume. The remainder of the capsule is filled with air or an inert gas, for example argon.

Figure 4A:
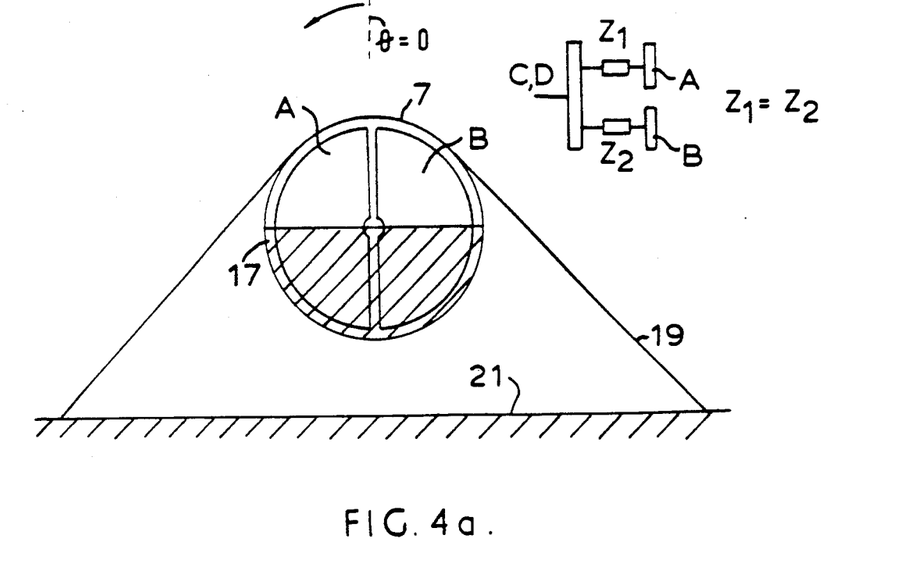
FIGS. 4A-B are sectional views similar to FIG. 2 of the capsule at different inclinations.
Figure 4B:
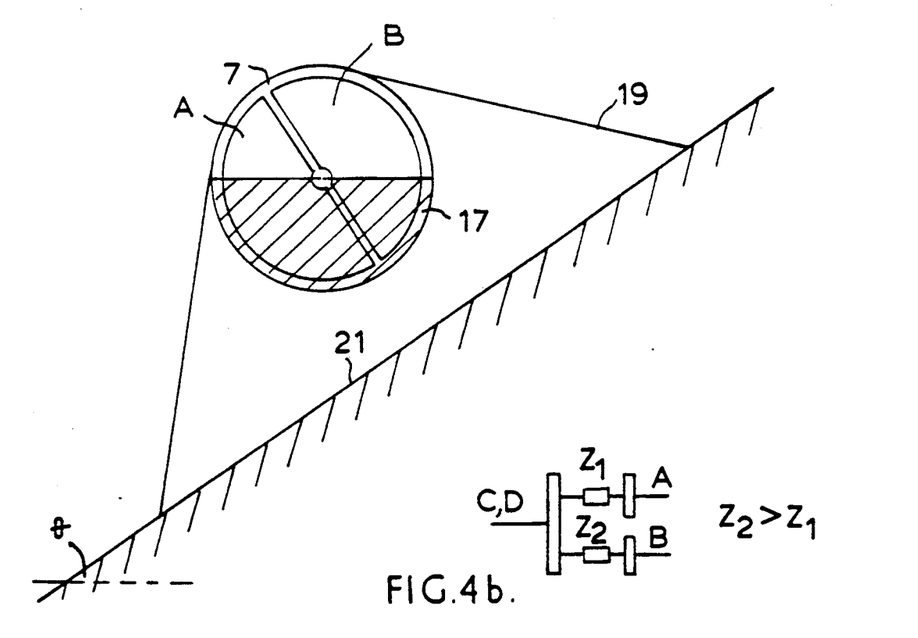

The general mode of operation of the capsule is described with reference to FIGS. 4A and 4B for which a measurement using electrodes A, B as the sensing electrodes is illustrated. FIGS. 4A and 4B illustrate the capsule 3 in a schematically shown mounting 19 having an edge 21 which is presented to a surface, the inclination of which is to be measured. One pair of electrodes in this case C, D are coupled together to form a common electrode and an alternating voltage is applied in turn to the electrodes A or B. The impedance and, more particularly, the resistance of the path between electrodes C, D and electrode A or electrode B is dependent upon the degree of immersion of electrode A or electrode B in the conductive liquid 17, the larger degree of immersion, the lower the resistance of the path.

Thus by measuring the resistances of the two paths, between electrodes C, D and electrode A and electrodes C, D and electrode B, the angle of inclination $\theta$ of the sensor can be calculated.

More specifically as can be seen by comparison of FIGS. 4A and 4B, the total wetted area of electrodes A, B is always substantially a constant, so that, ignoring cross impedances:

$$\frac{1}{Z_T} = \frac{1}{Z_1} + \frac{1}{Z_2}$$

where $Z_T$ = The total resistance of the capsule
$Z_1$ = The resistance of the path CD to A
$Z_2$ = The resistance of the path CD to B

AND $$Z_1 = \frac{180}{90 + \theta} \cdot Z_T \quad \text{1b}$$

$$Z_2 = \frac{180}{90 - \theta} \cdot Z_T \quad \text{1c}$$

So, the ratio, R, of the resistances Z1, Z2 is:

$$\frac{Z_1}{Z_2} = R = \frac{90 - \theta}{90 + \theta} \quad 2$$

hence $$\theta = 90 \frac{(1 - R)}{(1 + R)} \quad 3$$

Exemplary values of R are as follows:

TABLE 1

| $\theta$ | $R = \frac{Z_1}{Z_2}$ |
| --- | --- |
| −90 | ∞ |
| −50 | 3.5 |
| −45 | 3 |
| 0 | 1 |
| +45 | 0.33 |
| +50 | 0.286 |
| 90 | 0 |

Electrodes A, B are used for sensing angles up to ±50° from the horizontal in the configuration illustrated in FIGS. 4A and 4B. For angles of inclination greater than these limits, the electrodes may be reconfigured so that the electrodes A, B become the common electrode and the orthogonally disposed electrodes C, D become the sensing electrodes, the sensor measuring angles in this configuration in the range ±50° from vertical.

Reconfiguring the electrodes may conveniently be performed using a switch matrix comprising a plurality of analogue switches, for connecting each electrode to an alternating voltage source or to sensing circuitry in common with another electrode, as appropriate.

Figure 5:
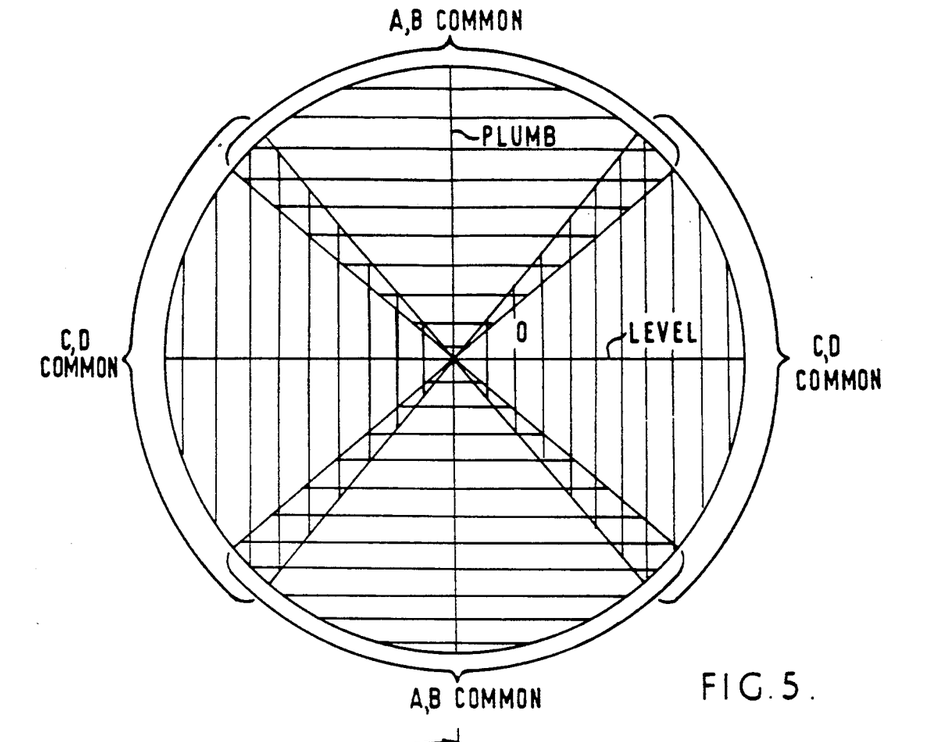
FIG. 5 illustrates the angular range of the sensor.

Use of such electrode switching allows a full 360° of inclination angle to be measured, in terms of deviation from level or plumb, (as shown in FIG. 5) with the electrode configuration being chosen by computing and control circuitry (not shown) in accordance with the angle of inclination of the sensor. When initialising an inclination measurement, the control circuitry may perform a measurement with an arbitrary pair of electrodes e.g. C, D chosen as the common pair. If the ratio R calculated by the computing circuitry is within an allowable range (±50°) (see Table 1), the measurement proceeds whereas if the measured ratio is outside the allowable range, the configuration is changed to connect the other pair of electrodes in common, and the measurement is then performed.

In the described capsule, the volume of the liquid 17 within the capsule 3 is prone to fluctuation with temperature. Due to volume changes arising from differing thermal expansion of the capsule and the liquid, changes in temperature will result in changes in liquid level which will affect the measurement of inclination. This effect is shown with reference to FIG. 6.

Figure 6:
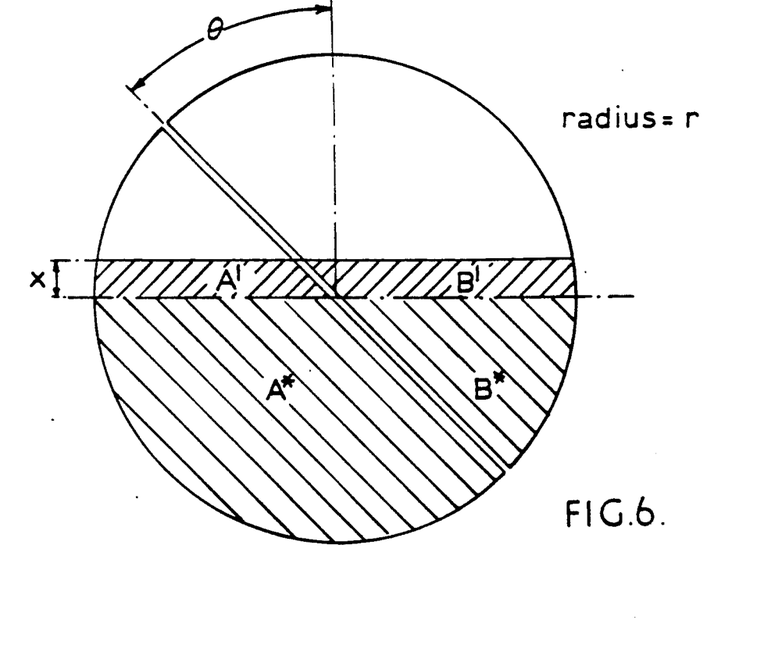
FIG. 6 is a diagram for explaining the effect of change in liquid level on capsule sensitivity.

Assuming an increase in liquid level, in response to temperature, is indicated by change in height x.

Then, let $S_T$ be the 'total' conductivity of the half filled capsule:

$$S_T = \frac{1}{Z_T} = \frac{1}{Z'_A} + \frac{1}{Z'_B} \qquad 4$$

where $Z_A'$, $Z_B'$ are the resistances of paths CD to A and CD to B.

$$\frac{1}{Z'_A} = S'_A = S_A* + S'_A \qquad 5$$

$$= \frac{S_T}{2}\left[1 + \frac{\theta}{90}\right] + \frac{S_T}{2}\left[\frac{xr}{\pi \frac{r^2}{4}}\right]$$

$$= \frac{S_T}{2}\left[1 + \frac{\theta}{90} + \frac{4x}{\pi r}\right] \qquad 6$$

where $S_A$ = the conductance due to plate area A immersed in the liquid
$S_{A'}$ = the conductance due to plate area A' immersed in the liquid Similarly $S'_B = \frac{S_T}{2}\left[1 - \frac{\theta}{90} + \frac{4x}{\pi r}\right] \qquad 7$ Now $R = \frac{S'_B}{S'_A} \qquad 8$ Combining 6, 7 and 8 and rearranging gives:

$$\theta = 90\left(\frac{1-R}{1+R}\right)\left(\frac{4x}{\pi r} + 1\right) \qquad 9$$

Hence a correction factor a is:

$$a = \left(1 + \frac{4x}{\pi r}\right) \qquad 10$$

Thus it can be seen that as x changes with temperature, the sensed angle will correspondingly change.

It can also be seen that if the capsule is not initially filled to exactly half its volume, an error which is dependent upon the consequent initial difference in liquid level will result, independently of any temperature induced change in liquid level. This may, however, be compensated for by calibration as described below.

Figure 7:
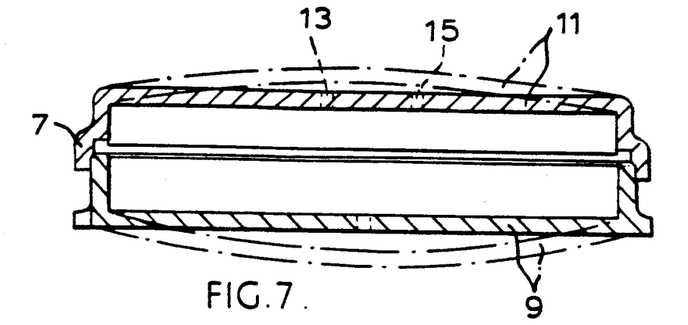
FIG. 7 illustrates the ability of the capsule shown in FIGS. 1 to 3 to compensate for temperature fluctuations.

In order to compensate for the change in level due to temperature, the sides 9, 11 of the capsule moulding 5, 7 are chosen to be of a thickness so as to be elastically deformable in response to change in pressure caused by change in volume of the liquid and change in gas vapour pressure within capsule 3 due to change in temperature as illustrated in FIG. 7 (for an increase in temperature). For a certain side thickness, the deformation of the sides 5, 7 will increase the volume of capsule 3 to match the increased volume of the liquid so as to keep the level of liquid 17 substantially constant, as illustrated by the following exemplary design calculations:

ASSUMPTIONS

1) That it is necessary to prevent (or reduce to negligible proportions) the variation in liquid level with temperature, within an hermetically sealed, part-filled, cylindrical vessel. (NB. the principle may be extended to non-cylindrical vessels).
2) That the liquid has a bulk coefficient of thermal expansion which is positive, and significantly greater than that of the vessel.
3) That the gas or vapour filling the remainder of the vessel displays a thermal variation of pressure which is essentially linear over the working temperature range.
4) That the vessel material is homogeneous, isotropic and has a single, positive value of thermal expansivity. (NB. The principle may still be employed if this assumption is not met, but the design calculations would become more involved).
5) For this particular design, the cylindrical vessel is mounted with the axis horizontal. The vessel walls are thin in relation to the vessel size and are not stressed beyond the elastic limit. All deflections are small.
6) The cylindrical vessel has a diameter D = 50 mm and an axial length L = 10 mm

DESIGN CALCULATIONS

Figure 8:
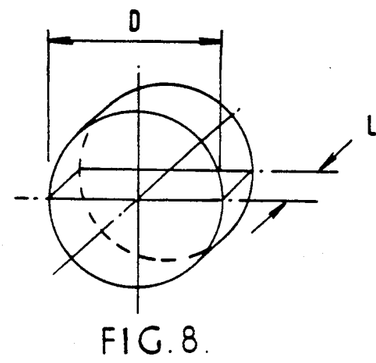
FIGS. 8 and 9 are diagrams illustrating features of the design calculations for calculating a preferred capsule wall thickness, for temperature compensation purposes.

1) Differential thermal expansion
Consider a cylindrical vessel of diameter D, of unit axial length and filled to a diameter with liquid of bulk thermal expansion coefficient $e_f$. The vessel is made of material having a linear expansion coefficient of $e_v$, as illustrated in FIG. 8.

The linear expansion coefficient is defined such that at temperature $T + \delta T$, $$\text{diameter} = D(1 + e_v \delta T)$$

and the bulk coefficient of the liquid similarly:

$$\text{volume} = V(1 + e_f \delta T)$$

where V = initial volume at temperature T.
Now vessel volume at T $$= \frac{\pi \cdot D^2}{4}$$

new volume at $T + \delta T$ $$= \frac{\pi}{4}[D(1 + e_v\delta T)]^2 (1 + e_v\delta T) \qquad (11)$$

$$= \frac{\pi D^2}{4}(1 + e_v\delta T)^3$$

Original liquid volume at $T$ $$= \frac{\pi D^2}{8}$$

New liquid volume $= \frac{\pi D^2}{8}(1 + e_f\delta T)$

∴ liquid rises in vessel by a height given by:—

$$\frac{\text{new liquid volume} - 1/2 \text{ of new vessel volume}}{\text{new } X\text{-sectional area at diameter}}$$

(NB. This assumes that variations in liquid level are small).

-continued

∴ liquid level rise $$= \frac{\frac{\pi D^2}{8}(1 + e_f\delta T) - \frac{\pi D^2}{8}(1 + e_v\delta T)^3}{D \cdot (1 + e_v\delta T)^2}$$

$$= \frac{\frac{\pi D}{8}[1 + e_f\delta T - (1 + e_v\delta T)^3]}{(1 + e_v\delta T)^2}$$

expanding, and neglecting powers of $e_f$ and $e_v$, $$= \frac{\frac{\pi D}{8}[e_f\delta T - 3e_v\delta T]}{1 + 2e_v\delta T} \quad (12)$$

which is approximately:

$$\frac{\pi D}{8} \delta T(e_f - 3e_v) \quad (13)$$

(since $2 \cdot e_v\delta T <<< 1$)

Note that $3 \cdot e_v$ = bulk expansion coefficient of the vessel.

Figure 9:
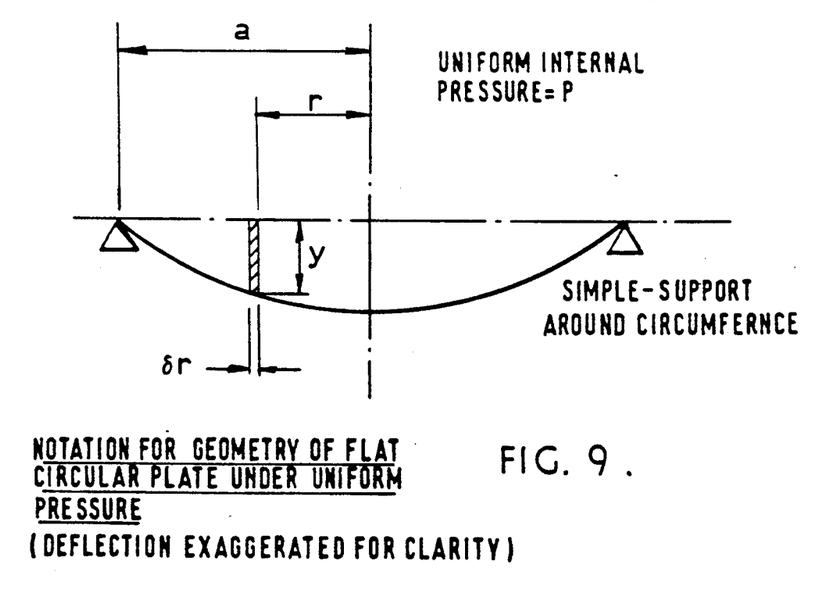

2) Vessel bulging due to internal pressure

For a flat circular plate, simply-supported at the circumference, the deflection at any point at radius r from the centre, is given by:

$$y = \frac{3 \cdot P a^2 (1 - V^2)}{8 E t^3} \left[ \frac{(5 + \nu) a^2}{2(1 + \nu)} + \frac{r^4}{2a^2} - \frac{(3 - \nu) r^2}{(1 + \nu)} \right] \quad (14)$$

(REF ROARK. Formulas for stress and strain (McGraw Hill, 4th Edition) Page 216, Case 1)
where
P = internal pressure
a = radius of plate
E = Youngs modulus of plate material
t = plate thickness
ν = poissons ration of plate material (assumes material is isotropic)

The incremental volume due to this deflection is given by:

$$2\pi \int_{r=o}^{r=a} y \cdot r \cdot dr \quad (15)$$

Assuming that pressure/temperature is given by the gas laws:

$$\frac{P_2}{P_1} = \frac{T_2}{T_1}$$

or $P_2 = P_1 \frac{T_2}{T_1}$ or $P = P_2 - P_1$ $$= P_1\left(\frac{T_2}{T_1} - 1\right)$$

$\frac{1}{293} P_1/K$ (for small temperature changes)

(Assuming that $T_1 = 20°$ C. = 293 K)

∴ bulge volume, as a function of temperature is given by:—

$$\frac{2\pi}{293} \cdot \frac{3}{8} \cdot \frac{P_1 a^2 (1 - \nu^2)}{E \cdot t^3} \int_{r=o}^{r=a} \left[ \frac{(5 + \nu)}{2(1 + \nu)} a^2 + \frac{r^4}{2a^2} - \frac{(3 + \nu)}{(1 + \nu)} r^2 \right] r \cdot dr \, (mm^3/K)$$

Substituting values:

$p_1$ = 0.1 N/mm² (= 1 bar)
$a$ = 25 mm
$\nu$ = 0.4 (for polyester · ref KEMPE'S.
$E$ = 2300 N/mm² (for VALOX material nominal value)

and integrating gives:—

$$\frac{2\pi}{293} \cdot \frac{3}{8} \cdot \frac{0.1 \cdot 25^2 \cdot 0.84}{2300 \, t^3} \int_0^{25} 1205r + \frac{r^5}{1250} - 2.429r^3 \, dr$$

$$= \frac{183.559}{10^6 \, t^3} \left[ \frac{1205r^2}{2} + \frac{r^6}{7500} - \frac{r^4}{1.6468} \right]_0^{25}$$

$$= \frac{31.56}{t^3} \, mm^3/K. \quad (16)$$

3) Equate thermal expansion to vessel bulging. Taking expansivity values of exemplary materials used:
For methanol: $e_f = 1190 \cdot 10^{-6}$ (BULK)
For VALOX: $e_v = 70 \cdot 10^{-6}$ (LINEAR) (nominal value)

Differential volume change due to thermal expansion
= liquid height change × diametral cross-section $$= \frac{\pi \cdot D}{8}(1190 - 3.70) \cdot 10^{-6} \cdot D \cdot L \text{ (from (13).)}$$

where $L$ = axial length of vessel = 10 mm.

$$= \frac{\pi \cdot 60^2 \cdot 10}{8 \cdot 10^6}(1190 - 210)$$

$= 9.621 \, mm^3/K$ $9.621 = \frac{31.56}{t^3}$ $t^3 = \frac{31.56}{9.621}$ $t = 1.486 \, mm$ The calculations assume that there is negligible pressure bulging of the cylindrical wall of the vessel and that both circular walls are of equal thickness.

The principle can still be employed if these assumptions are not met.

For ease of calculation, it has been assumed that the capsule walls are simply-supported at the circumference and of uniform thickness. More refined analysis may be carried out within the ability of one skilled in the art by, for example, finite element techniques to provide a more accurate determination of equation 14 for a particular application.

It is to be appreciated that this principle is usable in applications other than for the inclination sensor described.

The above compensation technique may be further employed to give added temperature compensation for other elements in the inclination sensor. More particularly, if the sensor is used to measure angles outside the range of electrodes AB by employing electrode switching to measure, for example, a full 360° of inclination angle as previously described, if electronic switches to perform the electrode switching formed as part of an application specific integrated circuit (ASIC), for example, are used for such switching, then the resistance of the switches will tend to change with temperature.

Such resistance contributes to the total resistance of the sensor as measured, and thus the computing and control circuitry needs to be calibrated to take the switch resistance into account (as described below). Such calibration cannot, however, compensate for temperature-induced resistance fluctuation, without the use of a temperature sensor and a sizable increase in calibration memory capacity.

Figure 10:
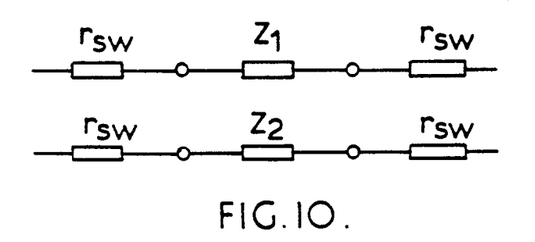
FIG. 10 is a diagram for explaining the effect of switch resistance on capsule sensitivity.

The effect of switch resistance on measured angle will be illustrated with reference to FIG. 10. For any usable electrode configuration, an analogue switch having a resistance $r_{sw}$ will be connected to each electrode, thus modifying the total sensed resistance ratio (R) of the capsule as follows:

$$R^{-1} = \frac{1}{R} = \frac{2r_{sw} + Z_2}{2r_{sw} + Z_1} \quad\quad 17$$

$$= \frac{2r_{sw} + \frac{2Z_T}{1 - \frac{\theta}{90}}}{2r_{sw} + \frac{2Z_T}{1 + \frac{\theta}{90}}} \quad\quad 18$$

(from equation 1b + 1c)

Expanding and rearranging, it can be shown that $$\theta^2 \left[ \frac{a(R^{-1} - 1)}{90^2} \right] + \quad\quad 19$$

$$\theta \left[ \frac{R^{-1} + 1}{90} \right] - (R^{-1} - 1)(1 + a) = 0$$

WHERE $a = \frac{r_{sw}}{Z_T} \quad\quad 20$

Solving as a quadratic equation in $\theta$ and letting:

$$\theta' = 90 \frac{(R^{-1} - 1)}{(R^{-1} + 1)} \quad\quad 21$$

$\left(\text{From equation 3, letting } R^{-1} = \frac{1}{R}, \right.$ $\theta'$ being the computed angle$)$ $$\theta = \frac{-1 \pm \sqrt{1 + 4a(1 + a)\left(\frac{\theta'}{90}\right)^2}}{\frac{2a}{90} \cdot \frac{\theta'}{90}} \quad\quad 22$$

As $\theta$ and $\theta'$ have the same sign, and since $a << 1$, using a Taylor expansion:

$$\theta = \frac{-1 + 1 + 2a(1 + a)\left(\frac{\theta'}{90}\right)^2}{\frac{2a}{90} \cdot \frac{\theta'}{90}} \quad\quad 23$$

$$= (1 + a)\theta'$$

The term $$\left(1 + \frac{r_{sw}}{Z_T}\right)$$

is dependent upon temperature due to fluctuation in $r_{sw}$ as mentioned above and also due to fluctuation in total capsule resistance $Z_T$. However it can be seen that the total angular-dependent compensation factor $a'$ for liquid level and for switch resistance is:

$$a' = 1 + \frac{4}{\pi} \cdot \frac{x}{r} + \frac{r_{sw}}{Z_T} \quad\quad 24$$

As previously discussed, the capsule can be designed to deform, to that $$\frac{4}{\pi} \cdot \frac{x}{r}$$

remains constant. However, the capsule can further be made to deform to compensate, to some extent for changes in $$\frac{r_{sw}}{Z_T},$$

so that the temperature dependence of the compensation factor $a'$ is reduced still further. In this case, the level of liquid in the capsule will fluctuate slightly with temperature in order to provide the additional compensation for the switch and liquid resistance change.

For example, the compensation factor $a'$ may be rewritten in temperature dependent form as:

$$a' = 1 + \frac{r_{s,20}(1 + \beta\Delta T)}{Z_{T,20}(1 + a\Delta T)} + \frac{4}{\pi} \cdot \frac{x}{r} \Delta T \quad\quad 25$$

where $\Delta T$ represents a change in temperature from the measured values of $r_{sw}$ and $Z_T$ at a given temperature (20° in this example) and $\chi$ is the temperature dependent change in liquid level in mm/K.

For perfect temperature compensation:

$$\frac{r_{s,20}(1 + \beta\Delta T)}{Z_{T,20}(1 + a\Delta T)} + \frac{4}{\pi} \cdot \frac{x}{r} \Delta T = \frac{r_{s,20}}{Z_{T,20}} \quad\quad 26$$

which gives:

$$x = \frac{r_{s,20} \, r}{Z_{T,20} \, \Delta T} \cdot \frac{\pi}{4} [1 - (1 + \beta\Delta T)(1 - a\Delta T)] \quad\quad 27$$

for small $a, \beta$ $$\approx \frac{\pi}{4} \cdot \frac{r_{s,20}}{Z_{T,20}} (a - \beta) r \text{ mm/K.} \quad\quad 28$$

α and β may be found by experimentation so that the desired value for χ may be calculated and the capsule geometry designed to provide the necessary compensation for the non-zero height change χ, in a similar manner to that described with reference to equations 11 to 16.

In general, the capsule can be designed to deform in response to temperature to maintain the electrical transfer function of the capsule and any external sensor circuitry independent of temperature or at least to provide a "best fit" over a desired temperature range. In such a case, the temperature dependence of a capsule could be established empirically and the capsule design modified to provide the most useful compensation, in the manner previously described.

As described above, initial conditions (independent of temperature induced change) exist in the capsule and sensor, and the capsule and sensor need to be calibrated to take these initial conditions into account.

In general, the angle sensed by the capsule described above and associated sensor circuitry ($\theta'$) is related to the actual angle of inclination ($\theta$) by the following expression:

$$\theta = C_0 + C_1\theta' + C_2\theta'^2 + C_3\theta'^3 + \ldots C_n\theta'^n \quad 29$$
$$= a^*\theta' + b \quad 30$$

where $a^* = C_1 + C_2\theta' + C_3\theta'^2 + \ldots C_n\theta'^{(n+1)}$    31
       $b = C_0$    32
       30

The calibration factors $a^*$ and b are dependent, to some extent, on the position of the electrodes within the capsule and any errors in the placement of the electrodes will result in changes in the calibration factors, so that different factors $a^*$, b usually exist for each pair of electrodes A, B or C, D.

The inventors have found that the dominant influence affecting calibration factor $a^*$ is related to the variation in initial liquid level with respect to the measuring electrodes which is linearly related to angle, as is apparent from equation 10. The coefficients $C_2$–$C_N$ are, consequently, small in comparison to $C_1$ for capsules with reasonable manufacturing tolerances.

Thus, it can be seen from equation 26 that with this approximation the actual angle $\theta$ is a linear function of sensed angle $\theta'$.

Thus, if $\theta$ is plotted against $\theta'$, the gradient of the resulting straight line will give $a^*$. Thus, by placing the capsule at two, known angles $\theta_1$, $\theta_2$ measuring the corresponding sensed angles $\theta_1'$, $\theta_2'$ will provide sufficient data for establishing the gradient of the straight line between these two points and so will give $a^*$.

Then by applying the initial condition that $\theta = \theta'$ at the origin (0°), b can then be calculated as follows:

$$0 = \theta = a^*\theta' + b \quad 33$$
$$\rightarrow b = -a^*\theta' \quad (\theta = 0)$$

As the calibration factor b is dependent upon the electrode-to-measuring surface relationship, if the capsule is inverted, the sign of the calibration parameter b needs to be changed to provide the appropriate compensation.

At the manufacturing stage, the values of $a^*$ and b may be stored in a programmable read only memory (PROM) for use by the computing and control circuitry when calculating the actual inclination angle.

When calculating $a^*$ for the capsule of FIG. 1, preferably the known angles are chosen as ±45°. This difference in angles is chosen as it will be appreciated that although the terms $C_2$–$C_N$ are small, they do have some effect upon the measurement of angle. By choosing actual angles at opposed ends of the available angular range of the pair of plates, and by forcing the resulting straight line graph through the origin ($\theta = \theta' = 0$ (equation 33)), a reasonable spread of calibration compensation is given over the whole sensing range.

It will be noted that electrode configuration of plates A, B (for example) is usable to measure either 0° or 180°, depending upon whether the inclination measuring surface 21 is upside down or the right way up. In order to distinguish between these two conditions (or any other equivalent condition) in which identical areas of electrodes A and B are immersed in the liquid and where the difference in angular position depends upon the disposition of the surface 21, additional information concerning which of the two possible angles the inclination the measuring device is inclined at may be obtained by measuring the same angle for electrodes C and D. It can be seen that the position of the liquid relative to plates C and D will be different for the two "equivalent" inclinations measurable using plates A and B.

For the electrode arrangement as shown in the capsule of FIGS. 1 and 8 the following relationship holds:

TABLE 3

| Measuring Electrodes | Range | Non Measuring Electrodes | Polarity of Angular Measurement for Non Measuring Electrodes |
|---|---|---|---|
| (i) A,B | 50° < $\theta$ < −50° | C,D | −ve |
| (ii) A,B | $\theta$ > 130°; $\theta$ < −130° | C,D | +ve |
| (iii) C,D | −140° < $\theta$ < −40° | A,B | −ve |
| (iv) C,D | 40° < $\theta$ < 140° | A,B | +ve |

This relationship may then be used to enable the computing circuitry to decide whether or not the factor b should be added or subtracted.

We claim:

1. A capsule, part filled with a liquid, the volume of the liquid varying as a function of temperature and the capsule being elastically deformable in response to temperature-induced pressure change within the capsule, so that the internal volume of the capsule is variable in dependence upon temperature and whereby dimensions and material of walls of the capsule are selected to provide (a predetermined relationship between the level of liquid within the capsule and temperature) that the level of liquid remains substantially constant with respect to temperature over a temperature range.

2. A capsule as claimed in claim 1 wherein the capsule is formed from plastics material.

3. A capsule as claimed in claim 2 wherein the plastics material is a polybutylene terephthalate.

4. A capsule as claimed in claim 2 wherein the plastics material is reinforced with glass beads.

5. A capsule as claimed in claim 1 wherein the liquid includes methanol.

6. A capsule as claimed in claim 1, wherein the capsule is formed as a hollow cylinder, the end walls of the cylinder being arranged to deform in response to said pressure change and the cylindrical side wall of the cylinder being arranged to be irresponsive to said change.

7. A capsule as claimed in claim 1 wherein the capsule comprises first and second mouldings connected together.

8. A capsule as claimed in claim 6 wherein the capsule comprised a hollow cylindrical member and first and second discs, each disc being connected to an end of the cylindrical member.

9. An inclination sensor including a capsule as claimed in claim 1 further comprising a plurality of electrodes connected to the capsule for sensing an electrical characteristic across the liquid said electrical characteristic varying in dependence upon the inclination of the capsule about a reference axis so that the sensor has an electrical transfer function which is a function of inclination angle.

10. A sensor as claimed in claim 9 wherein said predetermined relationship is selected to provide compensation for the dependence on temperature of said transfer function over a temperature range.

11. A sensor as claimed in claim 9 further comprising switch means for connecting the electrodes in a plurality of desired configurations, the switch means having an electrical transfer function which is a function of temperature.

12. A sensor as claimed in claim 11 wherein said predetermined relationship is selected to provide compensation for the dependence on temperature of the combined electrical transfer function of the capsule and switch means over a temperature range.

13. A sensor as claimed in claim 9 wherein said plurality of electrodes includes first and second electrodes disposed within the capsule, the relative degree of immersion of the first and second electrodes in the liquid being indicative, within a first angular range, of the angle of inclination of the capsule both about the reference axis and relative to a first reference condition.

14. A sensor as claimed in claim 13 wherein said plurality of electrodes further includes third and fourth electrodes disposed within the capsule, the relative degree of immersion of the third and fourth electrodes in the liquid being indicative, within a second angular range, of the angle of inclination of the capsule both about a reference axis and relative to a second reference condition different from the first reference condition.

15. A sensor as claimed in claim 14 wherein the first and second reference conditions are those at which the first and second electrodes or the third and fourth electrodes, respectively, are equally immersed in the liquid.

16. A sensor as claimed in claim 14 wherein the first to fourth electrodes are arranged so that any angle of inclination of the capsule about the reference axis is included within at least one of the first and second ranges.

17. A sensor as claimed in claim 14 wherein the first and second reference conditions are orthogonally disposed.

18. A sensor as claimed in claim 13 wherein the first and second electrodes are of substantially semi-circular form and are spaced one from the other about the reference axis.

19. A sensor as claimed in claim 14 wherein the third and fourth electrodes are of semi-circular form and are spaced one from the other about the reference axis.

20. An inclination measuring device including a sensor as claimed in claim 13, the sensor being mounted relative to a measuring surface disposed parallel to the first reference condition, so that inclination of the measuring surface results in corresponding inclination of the sensor capsule.

21. A capsule, part filled with a liquid, the walls of the capsule being formed so that a temperature-induced pressure change within the capsule will cause the walls of the capsule to deform elastically to maintain the level of the liquid in the capsule substantially constant.

22. A capsule as claimed in claim 21 wherein the capsule is formed from plastics material.

23. A capsule as claimed in claim 22 wherein the plastics material is a polybutylene terephthalate.

24. A capsule as claimed in claim 22 wherein the plastics material is reinforced with glass beads.

25. A capsule as claimed in claim 21 wherein the liquid comprises methanol.

26. A capsule as claimed in claim 21 wherein the capsule is formed as a hollow cylinder, the end walls of the cylinder being arranged to deform in response to said pressure change and the cylindrical side wall of the cylinder being arranged to be irresponsive to said change.

27. A capsule as claimed in claim 21 wherein the capsule comprises first and second mouldings connected together.

28. A capsule as claimed in claim 26 wherein the capsule comprises a hollow cylindrical member and (bit) first and second discs, each disc being connected to a respective end of the cylindrical member.

29. An inclination sensor including a capsule as claimed in claim 21.

30. A sensor as claimed in claim 29 wherein the capsule further includes a plurality of electrodes arranged for contact with the liquid.

31. A sensor as claimed in claim 30 wherein said plurality of electrodes includes first and second electrodes disposed within the capsule, the relative degree of immersion of the first and second electrodes in the liquid being indicative, within a first angular range, of the angle of inclination of the capsule both about a reference axis and relative to a first reference condition.

32. A sensor as claimed in claim 31 wherein said plurality of electrodes further includes third and fourth electrodes disposed within the capsule, the relative degree of immersion of the third and fourth electrodes in the liquid being indicative, within a second angular range, of the angle of inclination of the capsule both about a reference axis and relative to a second reference condition different from the first reference condition.

33. A sensor as claimed in claim 32 wherein the first and second reference conditions are those at which the first and second electrodes or the third and fourth electrodes, respectively, are equally immersed in the liquid.

34. A sensor as claimed in claim 31 wherein the first to fourth electrodes are arranged so that any angle of inclination of the capsule about the reference axis is included within at least one of the first and second ranges.

35. A sensor as claimed in claim 32 wherein the first and second reference conditions are orthogonally disposed.

36. A sensor as claimed in claim 31 wherein the first and second electrodes are of substantially semi-circular form and are spaced one from the other about the reference axis.

37. A sensor as claimed in claim 32 wherein the third and fourth electrodes are of semi-circular form and are spaced one from the other about the reference axis.

38. An inclination measuring device including a sensor as claimed in claim 31, the sensor being mounted relative to a measuring surface disposed parallel to the first reference condition, so that inclination of the measuring surface results in corresponding inclination of the sensor capsule.

39. A method of calibrating an inclination sensor of the form comprising a capsule part filled with a liquid, the position of the liquid within the capsule being indicative of the angle of rotation of the capsule about a reference axis, a plurality of electrodes disposed within the capsule for sensing said position within an angular range, an excitation source, a sensing circuit and means for connecting said electrodes to the sensing circuit and to the excitation source allow measurement of a plurality of electrical characteristics of the liquid which together are indicative of said position, said method comprising the steps of placing the sensor at least two known angles $\theta$, measuring the corresponding sensed angles $\theta'$ and calculating from the known and sensed angles calibration values a and b where:

$$\theta = a\theta' + b$$

40. A method as claimed in claim 39 wherein a is taken to be constant within at least one part of said angular range.

41. A method as claimed in claim 40 wherein b is taken to be equal to $-a\ \theta'$ at $\theta = 0$.

42. A method as claimed in claim 39 wherein the sensor includes a first pair of electrodes arranged to measure angles within a first said part of said angular range and a second pair of electrodes arranged to measure angles within a second said part of said angular range.

43. A method as claimed in claim 42 wherein said first part comprises a range of angles $\alpha$ and said first pair of electrodes are arranged to measure angles within a further part of said range, which comprises a range of angles $180° + \alpha$ and when in said further part, the said factor b is taken to be equivalent in magnitude but of opposite sign to the factor b of said first part.

44. A method as claimed in claim 42 wherein said second part comprises a range of angles $\beta$ and said second pair of electrodes are arranged to measure angles within a further range of angles $180° + \beta$ and when in said further part, the said factor b is taken to be equivalent in magnitude but of opposite sign to the factor b of said second part.

* * * * *